(12) United States Patent
Abraham et al.

(10) Patent No.: US 10,206,923 B2
(45) Date of Patent: Feb. 19, 2019

(54) PHARMACEUTICAL COMPOSITION OF ALOGLIPTIN AND METFORMIN

(71) Applicant: TORRENT PHARMACEUTICALS LIMITED, Ahmedabad (IN)

(72) Inventors: Jaya Abraham, Gandhinagar (IN); Suryakant Navale, Gandhinagar (IN); Pradip Mukhopadhyay, Gandhinagar (IN); Muzaffar Madny, Gandhinagar (IN)

(73) Assignee: Torrent Pharmaceuticals Limited, Ahmedabad, Gujarat (IN)

(*) Notice: Subject to any disclaimer, the term of this patent is extended or adjusted under 35 U.S.C. 154(b) by 0 days.

(21) Appl. No.: 15/753,523

(22) PCT Filed: Aug. 17, 2016

(86) PCT No.: PCT/IB2016/054913
§ 371 (c)(1),
(2) Date: Feb. 19, 2018

(87) PCT Pub. No.: WO2017/029609
PCT Pub. Date: Feb. 23, 2017

(65) Prior Publication Data
US 2018/0235966 A1 Aug. 23, 2018

(30) Foreign Application Priority Data
Aug. 20, 2015 (IN) .......... 3175/MUM/2015

(51) Int. Cl.
*A61K 31/513* (2006.01)
*A61K 9/20* (2006.01)
*A61K 31/155* (2006.01)
*A61K 45/06* (2006.01)

(52) U.S. Cl.
CPC .......... *A61K 31/513* (2013.01); *A61K 9/2018* (2013.01); *A61K 9/2077* (2013.01); *A61K 31/155* (2013.01); *A61K 45/06* (2013.01); *A61K 9/2054* (2013.01)

(58) Field of Classification Search
None
See application file for complete search history.

(56) References Cited

U.S. PATENT DOCUMENTS 8,900,638 B2 12/2014 Yamamoto et al.

FOREIGN PATENT DOCUMENTS

WO 2007033266 A2 3/2007

OTHER PUBLICATIONS

International Search Report from corresponding PCT/IB2016/054913 dated Dec. 15, 2016.

*Primary Examiner* — Brian J Davis
(74) *Attorney, Agent, or Firm* — Melissa M. Hayworth; E. Joseph Gess

(57) ABSTRACT

Present invention relates to a stable pharmaceutical composition comprising intimate mixture of alogliptin and metformin, and suitable pharmaceutically acceptable excipient/s; wherein metformin is present in about 3.3 parts or more parts by weight relative to 100 parts by weight of the total weight of part comprising alogliptin. Invention also encompasses various processes of preparing said pharmaceutical composition and its use in improving glycemic control in adults with type 2 diabetes mellitus.

14 Claims, No Drawings

PHARMACEUTICAL COMPOSITION OF ALOGLIPTIN AND METFORMIN

FIELD OF INVENTION

Present invention relates to a stable pharmaceutical composition comprising alogliptin and metformin with suitable pharmaceutically acceptable excipient/s; wherein alogliptin and metformin are in intimate mixture. Invention also encompasses various processes of preparing said pharmaceutical composition and its use in improving glycemic control in adults with type 2 diabetes mellitus.

BACKGROUND

Alogliptin, 2-({6[(3R)-3-aminopiperidin-1-yl]-3-methyl-2,4-dioxo-3,4-dihydropyrimidin-1(2H)-yl}methyl)benzonitrile, a dipeptidyl peptidase-4 (DPP-4) inhibitor, is an antidiabetic drug which is approved in US as monotherapy or combination therapy with other agents such as metformin, sulfonylurea, thiazolidinedione and insulin, for improving glycemic control in adults with type 2 diabetes mellitus.

Metformin, N,N-Dimethylimidodicarbonimidic diamide, is an anti-diabetic drug belonging to biguanide class and is approved in US for monotherapy or combination therapy with other agents such as sulfonylureas, thiazolidinediones, meglitinides, DPP-IV inhibitors and SGLT2 inhibitors, for improving glycemic control in adults with type 2 diabetes mellitus.

U.S. Pat. No. 8,900,638 discloses therapeutic combination for diabetes or obesity; comprising dipeptidyl peptidase (DPP-IV) inhibitor alogliptin or a salt thereof and Metformin HCl; wherein alogliptin or a salt thereof and metformin HCl are physically separated from each other to provide stability to the formulation. It further describes the solid composition wherein contact of alogliptin or a salt thereof and metformin HCl is inhibited by layering approaches or by forming granules of alogliptin or a salt thereof and metformin HCl separately using wet granulation process.

Composition of alogliptin and metformin is either associated with manufacturing complexities such as sticking with alogliptin and incompatibility of alogliptin and metformin with each other or some of the excipients, which affects stability and dissolution of the formulation. The available prior art though tried to overcome problem of decrease in preservation stability by following different method of manufacturing such as different layering approaches or formulating granules of alogliptin and metformin separately with purpose of inhibiting contact of alogliptin and metformin; these techniques with added steps are tedious leading to increased complexity of manufacturing. Thus, there still remains need for development of stable pharmaceutical composition of alogliptin and metformin devoid of processing troubles with ease of manufacturing.

Present invention provides a stable, bioequivalent composition of alogliptin and metformin which overcomes all the mentioned issues and is produced using robust, reproducible and easily scalable process.

SUMMARY OF THE INVENTION

One aspect of the present invention is to provide a stable pharmaceutical composition comprising intimate mixture of alogliptin and metformin with suitable pharmaceutically acceptable excipient/s.

Another aspect of the present invention is to provide a stable pharmaceutical composition comprising intimate mixture of alogliptin and metformin and a stabilizer with other suitable pharmaceutically acceptable excipient/s.

Another aspect of the present invention is to provide a stable pharmaceutical composition comprising alogliptin and metformin according to present invention prepared by one or more processes selected from direct compression, dry granulation and wet granulation.

Another aspect of the present invention is to provide process of preparation of pharmaceutical composition according to present invention.

Another aspect of the present invention is to provide use of pharmaceutical composition according to present invention for improving glycemic control in adults with type 2 diabetes mellitus.

DETAILED DESCRIPTION OF THE INVENTION

Present invention relates to a novel approach of providing pharmaceutical composition comprising intimate mixture of alogliptin and metformin which provides a stable composition with desired dissolution profile and thus a bioequivalent product.

The following paragraphs detail various embodiments of the invention. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent important aspects of the invention that may be taken in isolation and combined with other important aspects of the invention described elsewhere within this specification as a whole, and including the examples. The skilled person will appreciate that the invention extends to such combinations of features and that these have not been recited in detail here in the interests of brevity.

The use of the terms "a" and "an" and "the" and similar referents in the context of describing the invention (especially in the context of the following claims) are to be construed to cover both the singular and the plural, unless otherwise indicated herein or clearly contradicted by context.

The term "added" or "mixed" as used herein are to be interpreted inclusively, unless the context requires otherwise. That is, the use of these words may imply mixing or addition of one of the components/parts/excipient/mixture of excipients with other component/part/excipients.

Throughout this specification and the appended claims it is to be understood that the words "comprise", "have" and "include" and variations such as "comprises", "comprising", "having" "includes", "including" are to be interpreted inclusively, unless the context requires otherwise. That is, the use of these words may imply the inclusion of an element or elements not specifically recited.

The term "alogliptin" as used herein includes alogliptin in free form, its pharmaceutically acceptable salts and its isomers, enantiomers, polymorphs, hydrates and solvates or mixtures thereof. Preferably, alogliptin present in the composition according to present invention is alogliptin benzoate. Alogliptin present in the composition according to present invention can be in crystalline form or amorphous form. Particle size distribution (PSD-D90) of alogliptin used according to present invention is less than 500 microns; preferably D90 is less than 100 microns, more preferably D90 is less than 50 microns.

The term "metformin" as used herein includes metformin in free form or its pharmaceutically acceptable salts and its isomers, enantiomers, polymorphs, hydrates and solvates or mixtures thereof. Preferably, metformin present in the composition according to present invention is metformin hydrochloride.

The term "intimate mixture" as used herein means mixture prepared by physically mixing required quantity of alogliptin and metformin together, preferably by sifting or milling. The term "intimate mixing" as used herein means process of physically mixing alogliptin and metformin which promotes contact of active ingredients with each other.

The term "stable pharmaceutical composition" means pharmaceutical composition exhibiting total impurities not more than 1.0% at 40° C. and 75% RH, when stored in High Density Polyethylene (HDPE) container for one month.

The term "part comprising alogliptin" as used herein means powder, granules, pellets or beads comprising alogliptin and optionally one or more pharmaceutically acceptable excipient/s.

The terms "D90" as used herein means at least 90% of the particles respectively; have volume diameter in the specified range when measured by a suitable method for example laser diffraction using a Malvern Mastersizer® laser diffraction instrument.

Prior art discloses that physical separation is essential to prevent decrease in preservation stability of composition comprising alogliptin and metformin. It suggests that contact of alogliptin and metformin must be inhibited to obtain a stable pharmaceutical composition. Hence to achieve a stable pharmaceutical composition various process techniques which lead to physical separation of alogliptin and metformin are disclosed.

It was surprisingly found by inventors that opposed to disclosed in prior art, a stable pharmaceutical composition comprising alogliptin and metformin was achieved, even when alogliptin and metformin were mixed intimately.

The first embodiment of the present invention provides a stable pharmaceutical composition comprising intimate mixture of alogliptin and metformin with suitable pharmaceutically acceptable excipient/s.

Another preferred embodiment of the present invention provides a stable pharmaceutical composition comprising intimate mixture of alogliptin and metformin and a stabilizer with other suitable pharmaceutically acceptable excipient/s.

Another preferred embodiment of the present invention provides a stable pharmaceutical composition comprising intimate mixture of alogliptin and metformin; wherein metformin is present in about 3.3 parts or more parts by weight relative to 100 parts by weight of the total weight of part comprising alogliptin.

Another embodiment of present invention provides a stable pharmaceutical composition comprising intimate mixture of alogliptin and metformin; wherein metformin is present in about 3.3 parts to about 50.0 parts by weight, more preferably metformin is present in about 4.0 parts to about 35.0 parts by weight and most preferably metformin is present in about 4.5 parts to about 10.0 parts by weight; relative to 100 parts by weight of the total weight of part comprising alogliptin.

Thus, a preferred embodiment of the present invention provides a stable pharmaceutical composition comprising intimate mixture of alogliptin and metformin; wherein metformin is present in about 4.5 parts by weight relative to 100 parts by weight of the total weight of part comprising alogliptin.

Also, another preferred embodiment of the present invention provides a stable pharmaceutical composition comprising intimate mixture of alogliptin and metformin; wherein metformin is present in about 10.0 parts by weight relative to 100 parts by weight of the total weight of part comprising alogliptin.

It was surprisingly found by inventors that intimate mixing of alogliptin and metformin followed by addition of certain excipients; particularly stabilizers such as mannitol, sorbitol, isomalt, L-arginine, glycine and meglumine intragranularly leads to a stable pharmaceutical composition. Preferably stabilizer is mannitol, sorbitol or isomalt.

Thus, another preferred embodiment of the present invention provides a stable pharmaceutical composition comprising intimate mixture of alogliptin and metformin; wherein metformin is present in about 4.5 parts by weight relative to 100 parts by weight of the total weight of part comprising alogliptin and one or more pharmaceutically acceptable excipient(s) selected from mannitol, sorbitol, isomalt, L-arginine, glycine and meglumine.

Another preferred embodiment of the present invention provides a stable pharmaceutical composition comprising intimate mixture of alogliptin and metformin; wherein metformin is present in about 10.0 parts by weight relative to 100 parts by weight of the total weight of part comprising alogliptin and one or more pharmaceutically acceptable excipient(s) selected from mannitol, sorbitol, isomalt, L-arginine, glycine and meglumine.

A generalized embodiment of the present invention provides a stable pharmaceutical composition according to any of the embodiments, wherein said composition is prepared by one or more processes selected from wet granulation, dry granulation and/or direct compression.

A preferred embodiment of the present invention provides a stable pharmaceutical composition according to any of the embodiments, wherein said composition is prepared by one or more processes selected from wet granulation and/or dry granulation.

Said compositions prepared by wet granulation or dry granulation process may have intragranular component wherein said intragranular component comprises one or more active pharmaceutical ingredient and excipients selected from diluent, disintegrant, stabilizer and binder and an extra granular component. The Intragranular component further comprises of two or more distinct parts, wherein any of the two or more distinct parts can alternatively comprise intimate mixture of alogliptin with metformin and solely metformin. At least one of such distinct part is present in the form of granules, pellets or beads. Said granules, pellets or beads can be prepared by any known method of granulation such as wet granulation i.e. by rapid mixing under high shear or low shear or fluidized bed processing, melt granulation and the like or dry granulation or roller compaction. Wet granulation can be either aqueous or non aqueous using suitable solvent. Dry granulation may be carried out by slugging or by roller compaction. Any of the said granules can be combined with other pharmaceutically acceptable excipients, generally referred as extragranular component. Said extragranular component may be in the form of powder, granules, pellets or beads. Preferably said extragranular component is in the form of powder or granules. The extragranular component preferably comprises excipients selected from diluent, binder, disintegrant, lubricant and stabilizer and optionally an active pharmaceutical excipient.

Any of said intragranular or extragranular components as stated herein above may comprise alogliptin and/or metformin; preferably intragranular component comprises a part comprising alogliptin and metformin in intimate mixture and suitable pharmaceutically acceptable excipients and another part comprising metformin and suitable pharmaceutically acceptable excipients. Optionally, the extragranular component may further comprise metformin and suitable pharmaceutically acceptable excipients.

Intragranular component as stated herein above may comprise a part comprising alogliptin and metformin in intimate mixture and one or more suitable pharmaceutically acceptable excipient(s), particularly mannitol. Intragranular component may also comprise another part comprising metformin and one or more suitable pharmaceutically acceptable excipient(s), particularly sorbitol. Extragranular components may preferably comprise diluents, disintegrant, lubricant and/or stabilizer.

Thus, another embodiment of present invention provides a stable pharmaceutical composition comprising
1. Intragranular component comprising a part comprising alogliptin and metformin in intimate mixture and one or more pharmaceutically acceptable excipient(s) and another part comprising metformin and one or more pharmaceutically acceptable excipient(s) and
2. Extragranular component comprising one or more suitable pharmaceutically acceptable excipient(s).

In a preferred embodiment, present invention provides pharmaceutical composition comprising
1. Intragranular component comprising a part comprising alogliptin and metformin in intimate mixture and one or more pharmaceutically acceptable excipient(s); wherein metformin is present in about 3.3 parts or more parts by weight relative to 100 parts by weight of the total weight of part comprising alogliptin and another part comprising metformin and one or more pharmaceutically acceptable excipient(s) and
2. Extragranular component comprising one or more suitable pharmaceutically acceptable excipient(s).

In a most preferred embodiment, present invention provides pharmaceutical composition comprising
1. Intragranular component comprising a part comprising alogliptin and metformin in intimate mixture and one or more pharmaceutically acceptable excipient(s); wherein metformin is present in about 10.0 parts by weight relative to 100 parts by weight of the total weight of part comprising alogliptin and another part comprising metformin and one or more pharmaceutically acceptable excipient(s) and
2. Extragranular component comprising one or more suitable pharmaceutically acceptable excipient(s).

In yet another preferred embodiment, present invention provides pharmaceutical composition comprising
1. Intragranular component comprising a part consisting essentially of granules comprising alogliptin and metformin in intimate mixture and one or more pharmaceutically acceptable excipient(s) and another part consisting essentially of granules comprising metformin and one or more pharmaceutically acceptable excipient(s) and
2. Extragranular component comprising one or more diluent, disintegrant, lubricant or stabilizer.

Hence, a preferred embodiment, present invention provides pharmaceutical composition comprising:
1. Intragranular component comprising a part consisting essentially of granules comprising alogliptin and metformin in intimate mixture and microcrystalline cellulose, povidone and mannitol; wherein metformin is present in about 10.0 parts by weight relative to 100 parts by weight of the total weight of part comprising alogliptin and another part consisting essentially of granules comprising metformin and microcrystalline cellulose, povidone and sorbitol and
2. Extragranular component comprising microcrystalline cellulose, croscarmellose sodium and magnesium stearate.

Compositions according to present invention may additionally comprise one or more antidiabetic agent. The antidiabetic agent can be present in any of the intragranular or extragranular component/s as described in the present invention. Such antidiabetic agents can be selected from biguanide, sulfonyl urea, thiazolidinediones, DPP-IV inhibitors, and the like. Preferably, antidiabetic agent is pioglitazone or pharmaceutically acceptable salt thereof.

Composition according to present invention can be prepared by any known method as known to a skilled person. A generalized embodiment of present invention provides process of preparing compositions according to present invention.

Another embodiment of present invention provides process of preparation of the stable pharmaceutical composition comprising steps of:
1) Mixing alogliptin and metformin and optionally adding one or more pharmaceutically acceptable excipient to the obtained mixture.
2) Optionally granulating the mixture of step 1.
3) Granulating metformin and optionally one or more pharmaceutical excipient(s).
4) Mixing mixture of step 1 or granules of step 2 and 3 and optionally adding one or more pharmaceutical excipient(s).
5) Preparing pharmaceutical composition from the mixture obtained in step 4.

An embodiment of present invention provides process of preparing a stable pharmaceutical composition comprising steps of:
1. Mixing metformin and at least one pharmaceutically acceptable excipient.
2. Granulating the mixture of step 1 with granulating fluid to prepare granules
3. Mixing alogliptin and metformin and optionally one or more pharmaceutically acceptable excipient(s)
4. Mixing step 2 and 3 and optionally one or more pharmaceutical excipient(s).
5. Preparing pharmaceutical composition from the mixture obtained in step 4.

Another embodiment of present invention provides process of preparing a stable pharmaceutical composition comprising steps of:
1. Mixing alogliptin and metformin and optionally adding one or more pharmaceutically acceptable excipient to the obtained mixture.
2. Granulating the mixture of step 1 with granulating fluid comprising one or more binder(s) in one or more solvent(s).
3. Granulating metformin and optionally one or more pharmaceutical excipient(s) with granulating fluid comprising one or more binder in one or more solvent(s).
4. Mixing granules of step 2 and 3 and optionally adding one or more pharmaceutical excipient(s).
5. Preparing pharmaceutical composition from the mixture obtained in step 4.

Another embodiment of present invention provides process of preparing a stable pharmaceutical composition comprising steps of:
1. Mixing metformin and povidone
2. Granulating the mixture of step 1 with water.
3. Mixing alogliptin and metformin and adding microcrystalline cellulose, mannitol and croscarmellose sodium in said mixture.
4. Mixing step 2 and 3 and magnesium stearate.
5. Preparing pharmaceutical composition from the mixture obtained in step 4.

Another embodiment of present invention provides process of preparing a stable pharmaceutical composition comprising steps of:
1. Mixing alogliptin and metformin and adding mannitol to the obtained mixture.
2. Optionally adding L-arginine to the mixture obtained in step 1
3. Granulating mixture of step 1 or 2 with granulating fluid comprising aqueous solution of hydroxypropyl cellulose.
4. Granulating mixture of metformin and povidone with granulating fluid comprising water
5. Mixing granules of step 3 and step 4 and adding microstalline cellulose and croscarmellose sodium and magnesium stearate to the said mixture.
6. Preparing pharmaceutical composition from the mixture obtained from step 5.

Another preferred embodiment of present invention provides process of preparing a stable pharmaceutical composition comprising steps of
1. Mixing alogliptin and metformin and adding mannitol, povidone and microcrystalline cellulose to the obtained mixture.
2. Granulating the mixture of step 1 with granulating fluid comprising water.
3. Granulating mixture of metformin, povidone and microcrystalline cellulose with granulating fluid comprising water and sorbitol.
4. Mixing granules of step 2 and 3 and adding microcrystalline cellulose, croscarmellose sodium and magnesium stearate.
5. Preparing pharmaceutical composition from the mixture obtained in step 4

Another embodiment of present invention provides process of preparing a stable pharmaceutical composition comprising steps of
1. Mixing of alogliptin and about 3.3 parts or more parts by weight of metformin relative to 100 parts by weight of the total weight of part comprising alogliptin and adding one or more pharmaceutically acceptable excipient to the obtained mixture.
2. Optionally granulating the mixture of step 1.
3. Granulating the remaining quantity of metformin and one or more pharmaceutical excipient(s).
4. Mixing mixture of step 1 or granules of step 2 and 3 and adding one or more pharmaceutical excipient(s).
5. Preparing pharmaceutical composition from the mixture obtained in step 4.

In another embodiment, mixing of alogliptin and 10.0 parts by weight of metformin relative to 100 parts by weight of the total weight of part comprising alogliptin and adding of one or more pharmaceutically acceptable excipient is preferred.

Hence, a preferred embodiment of present invention provides process of preparing a stable pharmaceutical composition comprising steps of 1. Mixing of alogliptin and 10.0 parts by weight of metformin relative to 100 parts by weight of the total weight of part comprising alogliptin and adding mannitol, povidone and microcrystalline cellulose to the obtained mixture.
2. Granulating the mixture of step 1 with granulating fluid comprising water.
3. Granulating the remaining quantity of metformin and povidone and microcrystalline cellulose with granulating fluid comprising water and sorbitol.
4. Mixing granules of step 2 and 3 and adding microcrystalline cellulose, croscarmellose sodium and magnesium stearate.
5. Preparing pharmaceutical composition from the mixture obtained in step 4.

In a general embodiment present invention provides pharmaceutical composition prepared by process as described herein above.

In another general embodiment the present invention may further comprise a coating.

The pharmaceutical composition as described in the present invention may have functional or non-functional coating, preferably coating is non-functional coating. Non-functional coating comprises a film forming polymer and one or more excipients suitable for said coating such as film former, plasticizer, glidant, opacifier or colorant. Example and suitable amount of said excipient is known to a skilled person or as given in *Handbook of pharmaceutical excipients* (sixth edition, 2009).

It was observed that addition of one or more plasticizer/s or humectant/s in coating avoided the problem of logo bridging and peel off effect during tablet manufacturing. The plasticizer/s or humectant/s according to the present invention includes mannitol, sorbitol, xylitol, isomalt, liquid petrolatum, propylene glycol, glycerine, polyethylene glycol, polyethylene glycol monomethyl ether, acetyl tributyl citrate, acetyl triethyl citrate, castor oil, diacetylated monoglycerides, dibutyl sebacate, diethyl phthalate, triacetin, tributyl citrate or triethyl citrate; or mixtures thereof.

Hence, in yet another generalized embodiment, the present invention further comprises a coating comprising one or more plasticizer/s.

Pharmaceutically acceptable excipients according to any of the embodiment of present invention comprise diluent, disintegrant, binder, lubricant, pH adjuster/acidulant, stabilizer and/or mixtures thereof and the like.

Composition according to present invention may optionally further comprises one or more surfactant, glidant, coloring agent, flavoring agent, preservative, antioxidant and the like. Example and suitable amount of said optional excipient is known to a skilled person or as given in *Handbook of pharmaceutical excipients* (sixth edition, 2009).

A diluent according to present invention includes powdered cellulose, microcrystalline cellulose, silicified microcrystalline cellulose, starch, pre-gelatinized starch, dibasic calcium phosphate, dibasic sodium phosphate, tribasic sodium phosphate, calcium silicate, precipitated calcium carbonate; sugars such as dextrose, lactose or sucrose; sugar alcohols such as mannitol, sorbitol, xylitol, isomalt or erythritol; or mixtures thereof. Preferably diluent is selected from mannitol, microcrystalline cellulose, silicified microcrystalline cellulose, isomalt and pre-gelatinized starch. Pharmaceutical composition comprises diluent in the amount of 5.0-30.0% w/w of the total composition.

A disintegrant according to present invention includes calcium carboxymethyl cellulose and its salt including sodium or calcium salt, cross-linked carboxymethyl cellulose sodium (Croscarmellose sodium), cross-linked carboxymethyl cellulose calcium, cross-linked polyvinylpyrrolidone, sodium starch glycolate, pregelatinized starch; low substituted hydroxypropyl cellulose; or mixtures thereof. Preferably disintegrant is selected from croscarmellose sodium and cross-linked polyvinylpyrrolidone. Pharmaceutical composition comprises disintegrant in the amount of 0.5-5.0% w/w of the total composition.

A binder according to present invention includes polyvinyl alcohol, polyvinyl pyrrolidone (povidone), starch, pregelatinised starch; cellulose derivatives such as cellulose powder, microcrystalline cellulose, hydroxypropyl methylcellulose, ethyl cellulose, methyl cellulose, hydroxypropyl cellulose, hydroxyethyl cellulose, gelatin, zein, polymethacrylates, sodium alginate, gums, synthetic resins or mixtures thereof. Preferably binder is selected from hydroxypropyl cellulose, polyvinyl pyrrolidone and polyvinyl alcohol. Pharmaceutical composition comprises binder in the amount of 1.0-10.0% w/w of the total composition.

A lubricant according to present invention includes sodium stearyl fumarate, magnesium stearate, calcium stearate, zinc stearate, glyceryl dibehenate, stearic acid, hydrogenated castor oil, polyethylene glycol, magnesium silicate, sorbitan monostearate & sucrose monopalmitate or mixtures thereof. Preferably lubricant is selected from magnesium stearate and sodium stearyl fumarate. Pharmaceutical composition comprises lubricant in the amount of 0.5-3.0% w/w of the total composition.

A pH adjuster/acidulant according to present invention includes acetic acid, citric acid, carbonic acid, fumaric acid, phosphoric acid, tartaric acid or mixtures thereof. Preferably pH adjuster/acidulant is selected from acetic acid, citric acid and tartaric acid. Pharmaceutical composition comprises pH adjuster/acidulant in the amount of 1.0-10.0% w/w of the total composition.

A stabilizer is any pharmacologically acceptable excipient which stabilizes the said pharmaceutical composition and does not include stabilization by means of physical separation. A stabilizer according to present invention includes amino acids such as L-arginine, glycine and others; sugar and sugar alcohols such as mannitol, sorbitol, xylitol, isomalt, erythritol and others; alkalizing agents such as meglumine and others; cyclodextrins, tetrasodium edetate or mixtures thereof. Preferably stabilizer is selected from mannitol, sorbitol, isomalt, L-arginine, glycine and meglumine. Pharmaceutical composition comprises stabilizer in the amount of 0.1-10.0% w/w of the total composition.

A solvent for granulation used according to present invention includes water, acetone, methyl alcohol, ethyl alcohol, isopropyl alcohol, polyalcohols, methylene chloride, chloroform, dichloromethane, ether and the like or combination thereof. Preferably solvent selected is water.

Pharmaceutical compositions prepared according to present invention, comprises alogliptin in the amount of 0.9 to 5.0%, preferably 3.0%, most preferably 1.3% w/w of the total composition and metformin in the amount of 50.0 to 85.0%, preferably 70.0-80.0%, most preferably 77.0% w/w of the total composition.

A pharmaceutical composition according to present invention is a solid composition for immediate release for oral administration and it can be in the form of tablet, powder or capsule. Preferably, said composition is in the form of tablet for oral administration.

Another embodiment of present invention provides use of the composition prepared according to present invention for improving glycemic control in adults with type 2 diabetes mellitus.

The invention will be further illustrated by the following examples, however, without restricting its scope to these embodiments.

Example 1

| No | Ingredients | % w/w |
|---|---|---|
| | Intragranular Component Granules 1: | |
| 1 | Alogliptin benzoate | 1.31 |
| 2 | Metformin HCl | 0.57 |
| 3 | Mannitol | 3.40 |
| 4 | L-Arginine | 0.28 |
| 4 | Hydroxypropyl cellulose | 0.13 |
| 5 | Water | Q.S |
| | Granules 2: | |
| 6 | Metformin HCl | 76.35 |
| 7 | Povidone K30 | 3.98 |
| 8 | Water | Q.S |
| | Extraganular Component: | |
| 9 | Microcrystalline cellulose | 12.43 |
| 10 | Croscarmellose sodium | 0.77 |
| 11 | Magnesium stearate | 0.77 |
| | Total | 100.00 |

Intragranular Component: Alogliptin benzoate and Metformin HCl were mixed followed by sifting with mannitol and L-Arginine through 20# sieve. Obtained mixture was granulated with granulating fluid prepared by dissolving hydroxypropyl cellulose in water. The granules so obtained were dried and sized through 0.8 mm screen of oscillating granulator. Metformin HCl and povidone K30 were co-sifted through 24# sieve, mixed and granulated in rapid mixer granulator using water. The granules so obtained were dried and sized through 0.8 mm screen of oscillating granulator.

Extragranular Component: Both granules as obtained from above mentioned processes were mixed for 10 minutes. Microcrystalline cellulose and croscarmellose sodium were sifted through 30# sieve and mixed with blend of obtained granules. The obtained blend was lubricated with magnesium stearate and was compressed by rotary compression machine to form tablet.

Example 2

| No | Ingredients | % w/w |
|---|---|---|
| | Intragranular Component Granules 1: | |
| 1 | Alogliptin benzoate | 1.31 |
| 2 | Metformin HCl | 0.26 |
| 3 | Mannitol | 3.71 |
| 4 | L-Arginine | 0.28 |
| 4 | Hydroxypropyl cellulose | 0.13 |
| 5 | Water | Q.S |

-continued

| No | Ingredients | % w/w |
|----|-------------|-------|
| Granules 2: | | |
| 6 | Metformin HCl | 76.67 |
| 7 | Povidone K30 | 3.98 |
| 8 | Water | Q.S |
| Extraganular Component: | | |
| 9 | Microcrystalline cellulose | 12.12 |
| 10 | Croscarmellose sodium | 0.77 |
| 11 | Magnesium stearate | 0.77 |
| | Total | 100.00 |

Example 2 can be prepared following similar procedure as described in Example 1.

Examples 3 and 4

| No | Ingredients | Ex. 3 % w/w | Ex. 4 % w/w |
|----|-------------|-------------|-------------|
| Intragranular Component Granules 1: | | | |
| 1 | Alogliptin benzoate | 1.31 | 1.31 |
| 2 | Metformin HCl | 0.26 | 0.57 |
| 3 | Mannitol | 3.99 | 3.68 |
| 4 | Hydroxypropyl cellulose | 0.14 | 0.14 |
| 5 | Water | Q.S | Q.S |
| Granules 2: | | | |
| 6 | Metformin HCl | 76.67 | 76.35 |
| 7 | Povidone K30 | 6.00 | 3.99 |
| 8 | Water | Q.S | Q.S |
| Extragranular Component: | | | |
| 9 | Microcrystalline cellulose | 10.10 | 12.43 |
| 10 | Croscarmellose sodium | 0.77 | 0.77 |
| 11 | Magnesium stearate | 0.77 | 0.77 |
| | Total | 100.00 | 100.00 |

Intragranular Component: Alogliptin benzoate and Metformin HCl were mixed followed by sifting with mannitol through 20# sieve. Obtained mixture was granulated with granulating fluid prepared by dissolving hydroxypropyl cellulose in water. The granules so obtained were dried and sized through 0.8 mm screen of oscillating granulator. Metformin HCl and povidone K30 were co-sifted through 24# sieve, mixed and granulated in rapid mixer granulator using water. The granules so obtained were dried and sized through 0.8 mm screen of oscillating granulator.

Extragranular Component: Both granules as obtained from above mentioned processes were mixed for 10 minutes. Microcrystalline cellulose and croscarmellose sodium were sifted through 30# sieve and mixed with blend of obtained granules. The obtained blend was lubricated with magnesium stearate and was compressed by rotary compression machine to form tablet.

Examples 5

| No | Ingredients | % w/w |
|----|-------------|-------|
| Intragranular Component Granules 1: | | |
| 1 | Alogliptin benzoate | 1.32 |
| 2 | Metformin HCl | 0.62 |
| 3 | Microcrystalline Cellulose | 0.82 |
| 4 | Mannitol | 3.27 |
| 5 | Povidone | 0.19 |
| 6 | Water | Q.S |
| Granules 2: | | |
| 6 | Metformin HCl | 77.14 |
| 7 | Microcrystalline Cellulose | 2.33 |
| 8 | Povidone K30 | 4.03 |
| 9 | Sorbitol | 0.47 |
| 10 | Water | Q.S |
| Extragranular Component: | | |
| 11 | Microcrystalline cellulose | 8.26 |
| 12 | Croscarmellose sodium | 0.78 |
| 13 | Magnesium stearate | 0.78 |
| | Total | 100.00 |

Intragranular Component: Alogliptin benzoate and Metformin HCl were mixed followed by sifting with microcrystalline cellulose, mannitol and povidone K30 through 20# sieve. Obtained mixture was granulated with granulating fluid—water. The granules so obtained were wet milled, dried and sized through 1.0 mm screen of Quadro co-mill. Metformin HCl, povidone K30 and microcrystalline cellulose were co-sifted through 20# sieve, mixed and granulated in rapid mixer granulator using granulating fluid prepared by dissolving sorbitol in water. The granules so obtained were wet milled, dried and sized through 0.5 mm screen of oscillating granulator.

Extragranular Component: Total granules of 1 (x) and granules of 2 as obtained from above mentioned processes were mixed in the quantity of 1x and 3x, respectively and further co-sifted with microcrystalline cellulose and croscarmellose sodium through 20# sieve. The obtained blend was then sandwiched between remaining part of metformin HCl granules in blender and blended for 30 minutes. The obtained blend was lubricated with magnesium stearate and was compressed by rotary compression machine to form tablet.

The tablets of example 1, 3, 4 and 5 were exposed to following conditions:
40° C. and 75% RH for 1 month in HDPE container The impurity profile of the tablets was determined by Shimadzu High Performance Liquid Chromatograph using gradient method.

The following table provides the amount of total impurities at the initial stage, and at the end of 1 month.

| Examples | Initial | 40° C.; 75% RH (1 month) |
|----------|---------|--------------------------|
| Example 1 | BQL | 0.07% |
| Example 3 | BQL | 0.09% |
| Example 4 | 0.15 | 0.06% |
| Example 5 | BQL | BQL |

BQL: Below quantification limit

The invention claimed is:
1. A stable pharmaceutical composition comprising intimate mixture of alogliptin and metformin and optionally with pharmaceutically acceptable excipients; wherein met- formin is present in about 3.3 parts or more parts by weight relative to 100 parts by weight of the total weight of part comprising alogliptin.

2. The stable pharmaceutical composition as claimed in claim 1 comprising intimate mixture of alogliptin and metformin; wherein metformin is present in about 3.3 parts to about 50.0 parts by weight, relative to 100 parts by weight of the total weight of part comprising alogliptin.

3. The stable pharmaceutical composition as claimed in claim 1 comprising intimate mixture of alogliptin and metformin; wherein metformin is present in about 10.0 parts by weight relative to 100 parts by weight of the total weight of part comprising alogliptin.

4. The stable pharmaceutical composition as claimed in claim 1, further comprising a stabilizer.

5. The stable pharmaceutical composition as claimed in claim 4, wherein stabilizer is selected from the group consisting of mannitol, sorbitol, isomalt, L-arginine, glycine and meglumine.

6. A stable pharmaceutical composition comprising:
   1) intragranular component comprising a part comprising alogliptin and metformin in intimate mixture and one or more pharmaceutically acceptable excipient(s); and
   2) extragranular component comprising one or more suitable pharmaceutically acceptable excipient(s).

7. The stable pharmaceutical composition as claimed in claim 6, comprising:
   1) intragranular component comprising a part comprising alogliptin and metformin in intimate mixture and one or more pharmaceutically acceptable excipient(s); wherein metformin is present in about 3.3 parts or more parts by weight relative to 100 parts by weight of the total weight of part comprising alogliptin and another part comprising metformin and one or more pharmaceutically acceptable excipient(s); and
   2) extragranular component comprising one or more suitable pharmaceutically acceptable excipient(s).

8. A process of preparation of a stable pharmaceutical composition comprising intimate mixture of alogliptin and metformin, comprising:
   1) mixing alogliptin and metformin and optionally adding one or more pharmaceutically acceptable excipient to the obtained mixture;
   2) optionally granulating the mixture of step 1;
   3) granulating metformin and optionally one or more pharmaceutical excipient(s);
   4) mixing mixture of step 1 or granules of step 2, and 3 and optionally adding one or more pharmaceutical excipient(s); and
   5) preparing pharmaceutical composition from the mixture obtained in step 4.

9. The stable pharmaceutical composition according to claim 1, additionally comprising one or more antidiabetic agent.

10. The stable pharmaceutical composition as claimed in claim 1 comprising intimate mixture of alogliptin and metformin; wherein metformin is present in about 4.0 parts to about 35.0 parts by weight, relative to 100 parts by weight of the total weight of part comprising alogliptin.

11. The stable pharmaceutical composition as claimed in claim 1 comprising intimate mixture of alogliptin and metformin; wherein metformin is present in about 4.5 parts to about 10.0 parts by weight, relative to 100 parts by weight of the total weight of part comprising alogliptin.

12. The stable pharmaceutical composition as claimed in claim 2 further comprising a stabilizer.

13. The stable pharmaceutical composition according to claim 2, additionally comprising one or more antidiabetic agent.

14. The stable pharmaceutical composition according to claim 12, additionally comprising one or more antidiabetic agent.

* * * * *